(12) United States Patent
Werth

(10) Patent No.: US 8,973,889 B2
(45) Date of Patent: Mar. 10, 2015

(54) TUBE CLAMP

(75) Inventor: Albert A. Werth, Kewadin, MI (US)

(73) Assignee: Saint-Gobain Performance Plastics Corporation, Aurora, OH (US)

( * ) Notice: Subject to any disclaimer, the term of this patent is extended or adjusted under 35 U.S.C. 154(b) by 768 days.

(21) Appl. No.: 12/721,922

(22) Filed: Mar. 11, 2010

(65) Prior Publication Data

US 2010/0229354 A1 Sep. 16, 2010

Related U.S. Application Data

(60) Provisional application No. 61/159,994, filed on Mar. 13, 2009, provisional application No. 61/176,712, filed on May 8, 2009, provisional application No. 61/265,502, filed on Dec. 1, 2009.

(51) Int. Cl.
*F16K 7/04* (2006.01)
*F16L 55/10* (2006.01)
(Continued)

(52) U.S. Cl.
CPC ............. *F16L 55/10* (2013.01); *A61M 39/284* (2013.01); *A61M 39/285* (2013.01); *F16K 7/065* (2013.01); *F16K 7/06* (2013.01)
USPC ..................................... 251/10; 251/4; 251/9

(58) Field of Classification Search
CPC . A61M 39/284; A61M 39/28; A61M 39/283; F16K 7/063; F16K 7/065; F16L 55/10
USPC ......... 251/4, 7, 9, 10, 95, 101, 107, 108, 111, 251/114, 115; 128/885; 606/120, 151, 157; 24/134 N, 134 L
See application file for complete search history.

(56) References Cited

U.S. PATENT DOCUMENTS

| 850,731 A | 4/1907 | Christensen |
| 1,441,154 A | 4/1922 | Johnson |
| 2,622,837 A | 12/1952 | Goodman |

(Continued)

FOREIGN PATENT DOCUMENTS

| EP | 0 232 233 A1 | 8/1987 |
| FR | 1415508 A | 10/1965 |

(Continued)

OTHER PUBLICATIONS

Notification of Transmittal, International Search Report and Written Opinion dated Oct. 26, 2010 from the corresponding International Patent Application No. PCT/US2010/027077 filed Mar. 12, 2010.

*Primary Examiner* — John K Fristoe, Jr.
*Assistant Examiner* — Hailey K Do
(74) *Attorney, Agent, or Firm* — Abel Law Group, LLP; Chi Suk Kim

(57) ABSTRACT

Embodiments of a clamp for compressing a flexible tube are disclosed herein. In one such embodiment, the clamp includes a first member, a second member moveably coupled to the first member to move into and out of a clamping position to apply a compressive force to the tube, a locking member to hold the first and second members in the clamping position, a third member moveably retained between a pair of sidewalls of one of the first member and the second member, and a fourth member moveably coupled to one of the first member and the second member and engageable with the third member to apply an additional compressive force to the tube.

23 Claims, 9 Drawing Sheets

(51) Int. Cl.
*A61M 39/28* (2006.01)
*F16K 7/06* (2006.01)

(56) References Cited

U.S. PATENT DOCUMENTS

| | | | |
|---|---|---|---|
| 2,660,395 A * | 11/1953 | Mair et al. | 251/6 |
| 2,796,228 A * | 6/1957 | Kelly | 251/7 |
| 2,825,525 A | 3/1958 | Kellam | |
| 3,460,797 A * | 8/1969 | Allenbaugh, Jr. | 251/9 |
| 3,512,748 A | 5/1970 | Wilson | |
| 3,766,925 A | 10/1973 | Rubricius | |
| 3,915,167 A | 10/1975 | Waterman | |
| 4,049,301 A | 9/1977 | Schenk | |
| 4,091,815 A | 5/1978 | Larsen | |
| 4,247,076 A * | 1/1981 | Larkin | 251/7 |
| 4,442,994 A | 4/1984 | Logsdon | |
| 4,487,205 A | 12/1984 | Di Giovanni et al. | |
| 4,582,292 A * | 4/1986 | Glotzback et al. | 251/9 |
| 4,588,160 A | 5/1986 | Flynn et al. | |
| 4,736,925 A | 4/1988 | Kamstrup-Larsen et al. | |
| 4,942,886 A * | 7/1990 | Timmons | 128/885 |
| 4,944,485 A | 7/1990 | Daoud et al. | |
| 4,978,100 A * | 12/1990 | Peurifoy | 251/8 |
| 5,026,020 A | 6/1991 | Betush | |
| 5,152,497 A | 10/1992 | Bissell | |
| 5,154,704 A | 10/1992 | Archibald | |
| 5,203,056 A | 4/1993 | Funk et al. | |
| 5,226,892 A | 7/1993 | Boswell | |
| 5,238,218 A | 8/1993 | Mackal | |
| 5,271,649 A | 12/1993 | Gromotka | |
| 5,273,253 A | 12/1993 | Rogers | |
| 5,285,997 A * | 2/1994 | Chang | 251/95 |
| 5,318,546 A | 6/1994 | Bierman | |
| 5,351,932 A * | 10/1994 | von Herrmann | 251/4 |
| 5,588,634 A | 12/1996 | Nettekoven | |
| 5,713,912 A | 2/1998 | Porter | |
| 5,729,872 A | 3/1998 | Ginocchio | |
| 6,101,684 A | 8/2000 | Ginocchio | |
| 6,113,062 A | 9/2000 | Schnell et al. | |
| 6,173,926 B1 | 1/2001 | Elvegaard | |
| 6,234,448 B1 | 5/2001 | Porat | |
| 6,261,254 B1 | 7/2001 | Baron et al. | |
| 6,390,721 B1 | 5/2002 | Wilson, II et al. | |
| 6,422,529 B1 | 7/2002 | Adelberg | |
| 6,592,558 B2 | 7/2003 | Quah | |
| 6,644,618 B1 | 11/2003 | Balbo | |
| 6,676,091 B2 | 1/2004 | Hauer | |
| 6,679,529 B2 | 1/2004 | Johnson et al. | |
| 6,708,377 B2 | 3/2004 | Maunder | |
| 7,137,611 B2 | 11/2006 | Aulicino | |
| 7,284,137 B2 | 10/2007 | Clark et al. | |
| 7,284,731 B1 | 10/2007 | Johnson et al. | |
| D584,405 S | 1/2009 | Stephens | |
| 8,215,609 B2 * | 7/2012 | Kim | 251/8 |
| 2003/0188401 A1 | 10/2003 | Huang | |
| 2005/0119626 A1 | 6/2005 | Rahe-Meyer | |
| 2006/0169934 A1 | 8/2006 | Werth | |
| 2008/0051731 A1 | 2/2008 | Schweikert | |
| 2008/0290303 A1 | 11/2008 | Mackal | |

FOREIGN PATENT DOCUMENTS

| | | |
|---|---|---|
| JP | H07-100207 A | 4/1995 |
| JP | 2004267269 A | 9/2004 |
| KR | 100741994 B1 | 7/2007 |
| WO | 0137901 A1 | 5/2001 |
| WO | WO 2007107692 A1 * | 9/2007 |

* cited by examiner

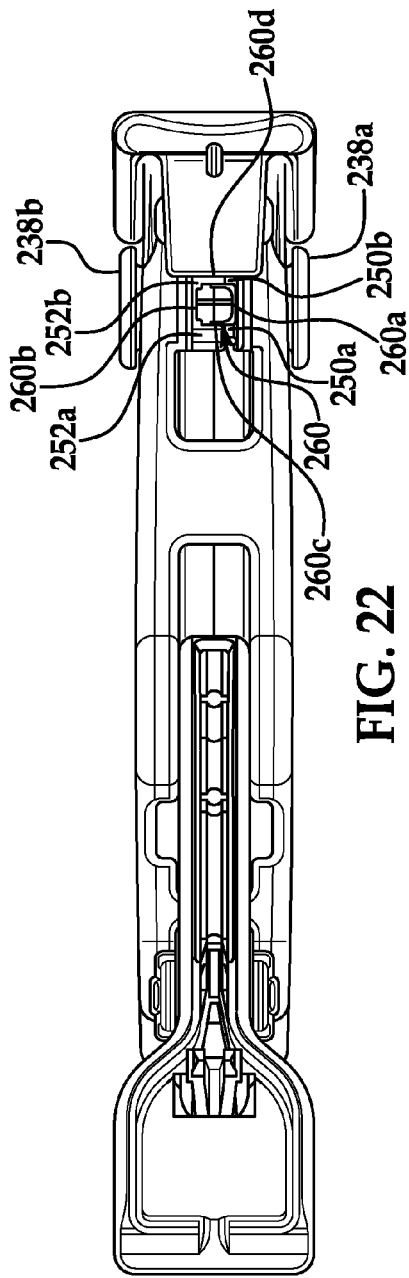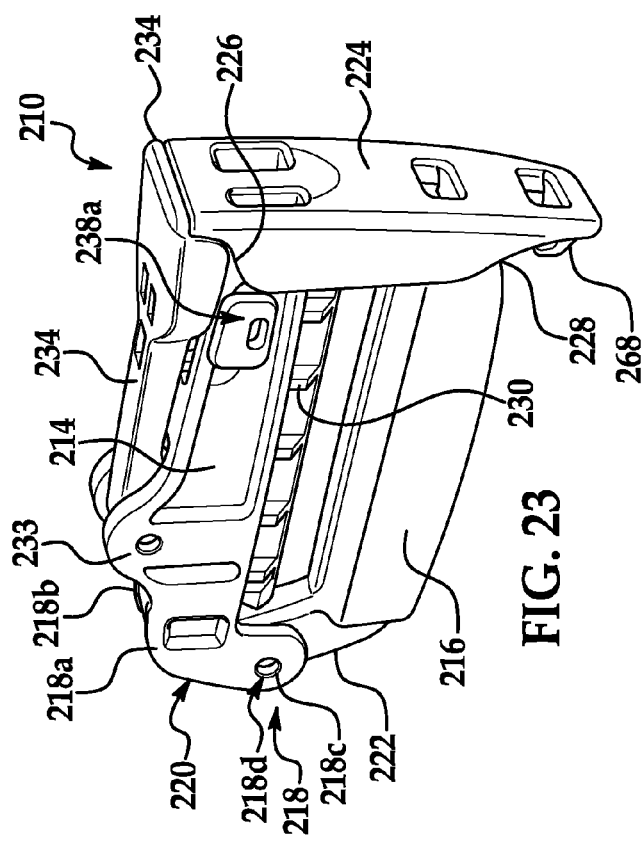

TUBE CLAMP

CROSS-REFERENCE TO RELATED APPLICATIONS

This application claims priority to U.S. Provisional Patent Application No. 61/159,994, filed Mar. 13, 2009, U.S. Provisional Patent Application No. 61/176,712, filed May 8, 2009, and U.S. Provisional Patent Application No. 61/265,502, filed Dec. 1, 2009, all of which are hereby incorporated by reference in their entirety.

FIELD OF THE INVENTION

The invention relates to a conduit clamp for closing a pathway defined by a conduit, and more particularly for closing a pathway defined by medical tubing.

BACKGROUND

Tubing, often made of a flexible material such as plastic or rubber, is widely used in the medical, pharmaceutical, biopharmaceutical, food and beverage and other laboratory environments. While the tubing typically serves as a conduit for fluid, occasionally it is useful to close the tubing, thereby stopping the flow of the fluid through the tube. To this end, various devices have been developed to close tubing. Many such devices include a moveable tube closing member having a portion engaged directly by a hand of a user to move the tube closing member into contact with the tubing and to close the tubing.

SUMMARY

Embodiments of a clamp for compressing a flexible tube are disclosed herein. In one such embodiment, the clamp includes a first member and a second member moveably coupled to the first member to move into and out of a clamping position to apply a compressive force to the tube. The clamp also includes a locking member to hold the first and second members in the clamping position and a third member moveably retained between a pair of sidewalls of one of the first member and the second member. Additionally, the clamp includes a fourth member fourth member moveably coupled to one of the first member and the second member and engageable with the third member to apply an additional compressive force to the tube.

In another such embodiment, the clamp includes a first member having a first end and a second end and a second member with a first end and a second end. The first and second members are moveably coupled at their first ends to move into and out of a clamping position to apply a compressive force to the tube. The clamp also includes a locking member pivotally coupled to the second end of at least one of the first member and second member. The locking member is adapted to hold the first and second members in the clamping position. Additionally, the clamp includes a lever member moveably coupled to one of the first member and the second member to apply an additional compressive force to the tube.

These and other embodiments are described in additional detail hereinafter.

BRIEF DESCRIPTION OF THE DRAWINGS

The description herein makes reference to the accompanying drawings wherein like reference numerals refer to like parts throughout the several views, and wherein:

FIG. 22 is a top plan view of the clamp of FIG. 21A without the tube;

FIG. 23 is a perspective view of the clamp of FIG. 21A in a fully engaged position without the tube;

DETAILED DESCRIPTION

Tubing in the medical and pharmaceutical industries has recently become larger. For example, tubing having a 1.5" outer diameter with a 0.25" wall thickness is now commonly used. Such tubing may be difficult to compress an amount sufficient to close the tubing by hand using known devices. Indeed, closing such tubing using known devices can require using a large amount of one's body weight.

Figure 1:
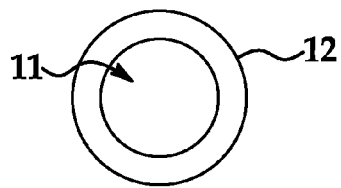
FIG. 1 is a side elevation view of an example of a tube.

A tube 12 as shown in FIG. 1 can define a fluid pathway 11. The tube 12 can be any type of tubing, such as tubing used in the medical or pharmaceutical industries for selectively controlling the flow of fluid. The tube 12 can also any other type of flexible tubing such as those used in irrigation or a garden hose. The tube 12 can be in communication with a manifold system, a bio-bag, a patient, and/or another object. Additionally, the tube 12 can be resilient such that it automatically re-opens from a closed position when not urged shut. As shown in FIG. 1, the tube 12 can have an outer diameter of 1.5" and an inner diameter of 1.0", though the tube 12 can have a different outer and/or inner diameter.

Figure 2:
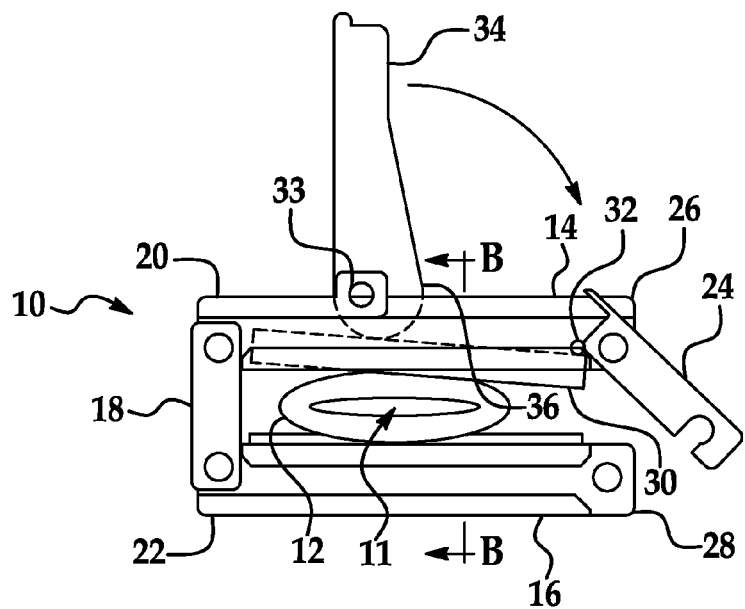
FIG. 2 is a side elevation view of an example of a tube clamp partially closing the tube of FIG. 1.
Figure 3:
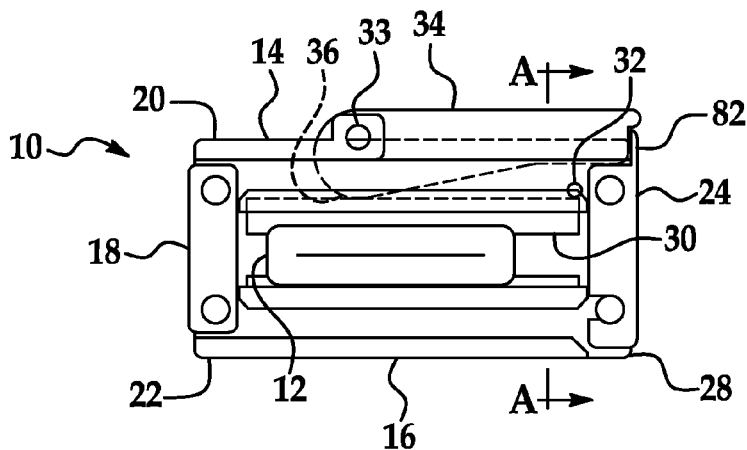
FIG. 3 is a side elevation view of the clamp of FIG. 2 fully closing the tube.

A clamp 10 as shown in FIGS. 2 and 3 can be used for closing the fluid pathway 11 through the tube 12. As a general overview of the clamp 10, the clamp 10 can include a top member 14 and a bottom member 16 as shown in FIGS. 2 and 3. A first link 18 can be pivotally coupled to a first end 20 of the top member 14 and a first end 22 of the bottom member 16. A second link 24 can be pivotally coupled to a second end 26 of the top member 14, and the second link 24 can be selectively engaged with a second end 28 of the bottom member 16.

When the second link 24 is not engaged with the bottom member 16 as shown in FIG. 2, the top member 14 can be rotated relative to the bottom member 16. To engage the clamp 10 with the tube 12, the top member 14 can be rotated away from the bottom member 16 such that there is a sufficient distance between the top and bottom members 14 and 16 to insert the tube 12 there between. With the top and bottom members 14 and 16 rotated sufficiently apart from one another, the clamp 10 can be moved to position the tube 12 between the top and bottom members 14 and 16, and then the top member 14 can be rotated toward the bottom member 16 to the position shown in FIGS. 2 and 3.

During rotation of the top member 14 toward the bottom member 16, the top member 14 can initially contact the tube 12, at which time the tube 12 is still fully open. When the top member 14 initially contacts the tube 12, the top member 14 can be angled obliquely relative to the bottom member 16 (i.e., the top member 14 can be angled away from the bottom member 16 relative to the position of the top member in FIG. 2). By further rotating the top member 14 toward the bottom member 16, the tube 12 can be initially deformed, thereby narrowing but not fully closing the pathway 11. Due to the geometry and construction of the tube 12, rotation of the top member 14 toward the bottom member 16 to initially deform the tube 12 can require a relatively small amount of force and can be accomplished by hand without a great deal of effort. For example, the top member 14 can be rotated by hand without applying one's body weight to a position in which the tube 12 is partially closed as shown in FIG. 2. As such, a mechanical advantage can be employed such that the force applied to the tube is a multiple of the force applied by hand to the lever. Therefore, even if a large force is required to close the tubing, the amount of force a user must input to the lever to close the tubing can be low.

As the top member 14 is rotated further toward the bottom member 16 from the position in which the top member 14 initially contacts the tube 12, the pathway 11 is narrowed. However, since the tube 12 can exert greater and greater amounts of force in opposition to rotation of the top member 14 toward the bottom member 16 as the tube 12 is narrowed, rotation of the top member 14 toward the bottom member 16 can eventually require a sufficiently large amount of force that continued rotation of the top member 14 toward the bottom member 16 by hand becomes difficult even though the tube 12 is not fully closed. The amount of force can be especially large when the tube 12 is of the oversized variety (e.g., having the 1.5" outer diameter and 1.0" inner diameter as shown in FIG. 1). With the clamp 10, however, the top member 14 need not be rotated until it is sufficiently close to the bottom member 16 to fully close the tube 12.

Instead, the top member 14 can be rotated toward the bottom member 16 only until the top member 14 is generally parallel with the bottom member 16 as shown in FIGS. 2 and 3, as deforming the tube 12 to allow the top and bottom members 14 and 16 to be parallel can still require a small enough amount of force to be performed by hand. With the top member 14 and bottom member 16 generally parallel, the second link 24 can be engaged with the bottom member 16 as shown in FIG. 3 to hold the top and bottom members 14 and 16 in the parallel position.

With the top and bottom members 14 and 16 held parallel to one another, a guillotine 30 can be actuated to fully close the tube 12 as shown in FIG. 3. (Note that the use of the word "guillotine" to describe guillotine 30 does not imply that the guillotine 30 cuts through the tube 12.) The guillotine 30 can be hinged to the top member 14 by a hinge 32 positioned near the second end 26 of the top member 14, and the top member 14 can include another hinge 33 to which a lever 34 having a cam portion 36 is rotatably coupled. The lever 34 can be actuated by rotating the lever 34 toward the top member 14, thereby causing the cam portion 36 to engage the guillotine 30 and urge the guillotine 30 downward from the position shown in FIG. 2 to the position shown in FIG. 3 to fully close the tube 12.

To disengage the clamp 10, the lever 34 can be rotated away from the top member 14, thereby disengaging the cam portion 36 from the guillotine 30. If resilient, the tube 12 can urge the guillotine 30 upward from the closed state shown in FIG. 3 to the open state shown in FIG. 1. The second link 24 can be disengaged from the bottom member 16, and the top member 14 can be rotated away from the bottom member 16.

Figure 4:
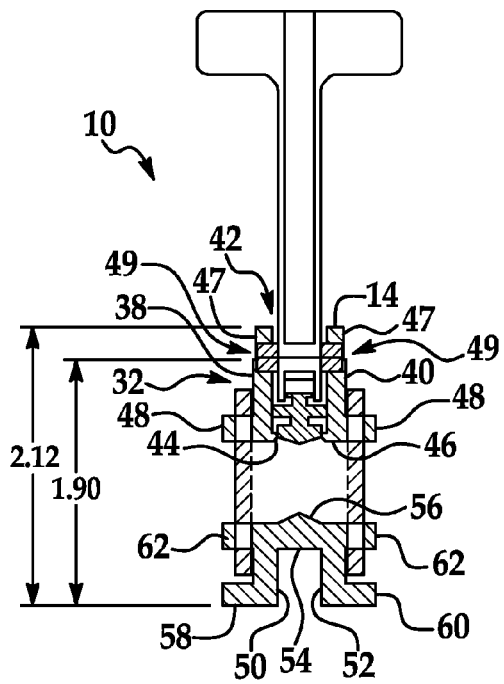
FIG. 4 is a cross-section of the clamp taken along line B-B of FIG. 2 without the tube.
Figure 5:
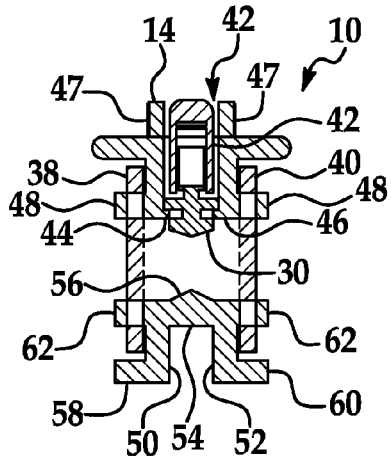
FIG. 5 is a cross-section of the clamp taken along line A-A of FIG. 3 without the tube.

Now describing the clamp 10 in detail with reference to FIGS. 4 and 5, the top member 14 can include a first sidewall 38 and a second sidewall 40. The sidewalls 38 and 40 can be generally parallel, and the sidewalls 38 and 40 can be spaced apart to define a channel 42 having a width slightly greater than a width of the guillotine 30. Thus, the guillotine 30 can move upward and downward between the sidewalls 38 and 40, as can be understood from FIGS. 4 and 5. A first lip 44 can extend from the first sidewall 38 toward the second sidewall 40, while a second slip 46 can extend from the second sidewall 40 toward the first sidewall 38. The lips 44 and 46 can be spaced apart by a distance less than the width of the guillotine 30. Thus, the lips 44 and 46 can limit movement of the guillotine 30 in a direction downward toward the bottom member 16 as shown in FIG. 5.

The top member 14 can additionally include four pins 48, with one pin 48 projecting perpendicularly from the first end 20 of the first sidewall 38 in a direction away from the second sidewall 40, a second pin 48 projecting perpendicularly from the second end 26 of the first sidewall 38 in a direction away from the second sidewall 40, a third pin 48 projecting perpendicularly from the first end 20 of the second sidewall 40 in a direction away from the first sidewall 38, and a fourth pin 48 projecting perpendicularly from the second end 26 of the second sidewall 40 in a direction away from the first sidewall 38. Additionally, each of the first and second sidewalls 38 and 40 can include an upwardly extending flange 47 defining an aperture 49. The flanges 47 can be spaced along the length of the top member 14 from the hinge 32, with the distance between the flanges 47 and the hinge 32 affecting the mechanical advantage provided by the lever 34.

The bottom member 16 can include a first sidewall 50 and a second sidewall 52 parallel to and spaced apart from the first sidewall 50. A platform 54 can extend between the first and second sidewalls 50 and 52, and a V-shaped ridge 56 can extend a length of the platform 54. A first foot 58 can run a length of the first sidewall 50, and the first foot 58 can extend away from the second sidewall 52. A second foot 60 can run a length of the second sidewall 52, and the second foot 60 can extend away from the first sidewall 50. The feet 58 and 60 can provide stability for the clamp 10 when the clamp 10 rests on a desk or other surface. The bottom member 16 can additionally include four pins 62, with one pin 62 projecting perpendicularly from the first end 22 of the first sidewall 50 in a direction away from the second sidewall 52, another pin 62 projecting perpendicularly from the second end 28 of the first sidewall 50 in a direction away from the second sidewall 52, a third pin 62 projecting perpendicularly from the first end 22 of the second sidewall 52 in a direction away from the first sidewall 50, and a fourth pin 62 projecting perpendicularly from the second end 28 of the second sidewall 52 in a direction away from the first sidewall 50.

Figure 6:
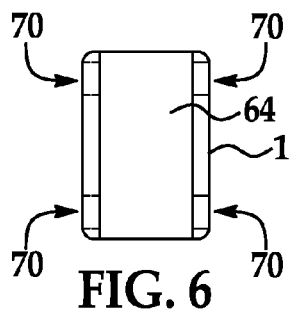
FIG. 6 is an end elevation view of a first link of the clamp of FIG. 2.
Figure 7:
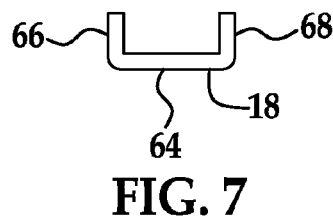
FIG. 7 is a top plan view of the first link of FIG. 6.
Figure 8:
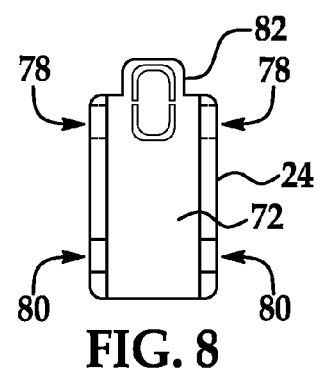
FIG. 8 is an end elevation view of a second link of the clamp of FIG. 2.
Figure 9:
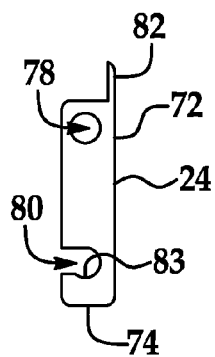
FIG. 9 is a side elevation view of the second link of FIG. 8.
Figure 10:
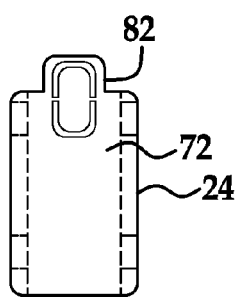
FIG. 10 is elevation view of the second link of FIG. 8 taken from an opposing end of the second link from the view of FIG. 8.
Figure 11:
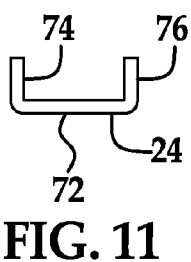
FIG. 11 is a top plan view of the second link of FIG. 8.

As shown in FIGS. 6 and 7, the first link 18 can include a backwall 64 and first and second sidewalls 66 and 68, respectively, extending parallel to one another and generally perpendicular to the backwall 64 from opposing longitudinal edges of the backwall 64. Each sidewall 66 and 68 can define two first apertures 70, with the apertures 70 near opposing longitudinal ends of the sidewalls 66 and 68.

To rotatably couple the first link 18 to the top member 14, the pins 48 and 62 projecting from the first end 20 of the top member 14 are inserted into the top apertures 70 in the first and second sidewalls 66 and 68, respectively, of the first link 18. Similarly, to rotatably couple the first link 18 to the bottom member 16, the pins 48 and 62 projecting from the first end 22 of the bottom member 14 are inserted into the bottom apertures 70 in the first and second sidewalls 66 and 68, respectively. These insertions can be accomplished by forming the first link 18 from a resilient material and snapping the first link 18 onto the top member 14 and bottom member 16.

As shown in FIGS. 8-11, the second link 24 can include a backwall 72 and first and and second sidewalls 74 and 76, respectively, extending parallel to one another and generally perpendicular to the backwall 72 from opposing longitudinal edges of the backwall 72. A tab 82 can extend from a top end of the backwall 78. Each sidewall 74 and 76 can define an aperture 78 near the tab 82 and a slot 80 opening to a side of the sidewalls 74 or 76 opposite the backwall 72 near an end of the second link 24 opposite the tab 82.

To rotatably couple the second link 24 to the top member 14, the pins 48 and 62 projecting from the second end 26 of the top member 14 are inserted into the apertures 78 of the first and second sidewalls 74 and 76, respectively, of the second link 24. To engage the second link 24 with the bottom member 16 as shown in FIG. 3, the second link 24 is rotated relative to the top member 14 toward the bottom member 16 until the pins 48 and 62 projecting from the second end 28 of the bottom member 16 are disposed in the slots 80 of the second link 24. The tube 12, if resilient, will be deformed between the top and bottom members 14 and 16 as shown in FIG. 2, and the tube 12 can thus exert of force urging the top and bottom members 14 and 16 away from each other. However, when the top member 14 is urged away from the bottom member 16 and vice versa, at least one of the pins 48 and 62 projecting from the second end 28 of the bottom member 16 contacts a bottom edge 83 of each slot 80 shown in FIG. 9, thereby preventing movement of the top member 14 away from the bottom member 16. The force between the pins 48 and 62 projecting from the second end 28 of the bottom member 16 and the bottom edges 83 of the slots 80 can produce a friction force that aids the engagement between the second link 24 and bottom member 16. With the second link 24 engaged with the bottom member 16, the tab 82 can extend upward as shown in FIG. 3.

Figure 17:
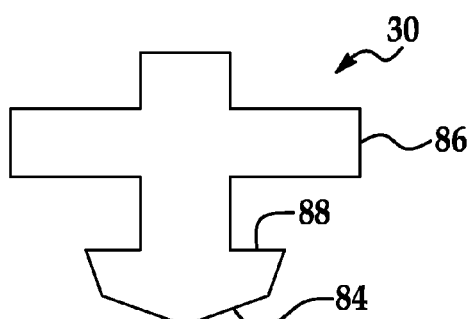
FIG. 17 is an end elevation view of a guillotine of the clamp of FIG. 2.

Referring now to FIG. 17, the guillotine 30 can have a V-shaped edge 84, which can face the V-shaped rib 56 of the platform 54 of the bottom member 16 as shown in FIG. 5. The V-shaped edge 84 and V-shaped rib 56 can act to create a high pressure location on the tube 12 when the clamp 10 is engaged with the tube 12, thereby reducing the amount of force required to deform the tube 12. Referring again to FIG. 17, the guillotine 30 can additionally include a longitudinally extending cross-bar 86 above a lower portion 88 of the guillotine 30 that includes the V-shaped edge 84. The width of the lower portion 88 can be less than the distance between the first and second lip 44 and 46 of the top member 14, thereby allowing the lower portion 88 to move below the lips 44 and 46 as shown in FIG. 5. The cross-bar 86, however, can have a greater greater width than the distance between the first and second lips 44 and 46 such that the lips 44 and 46 limit the downward movement of the guillotine 30. The guillotine 30 can be coupled to the hinge 32 as shown in FIGS. 2 and 3, which can be a pin passing through both the guillotine 30 and the top member 14. The hinge 32 can limit upward movement of the portion of the guillotine 30 engaged with the hinge 32.

Figure 12:
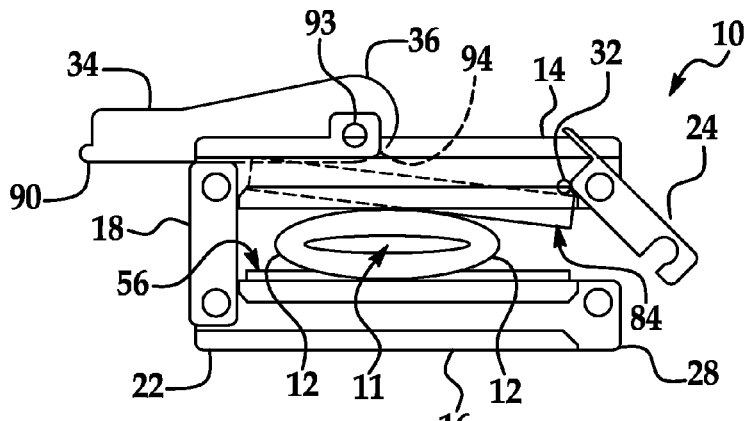
FIG. 12 is a side elevation view of the clamp of FIG. 2 having its second link disengaged from its bottom member and its lever in a released position.
Figure 13:
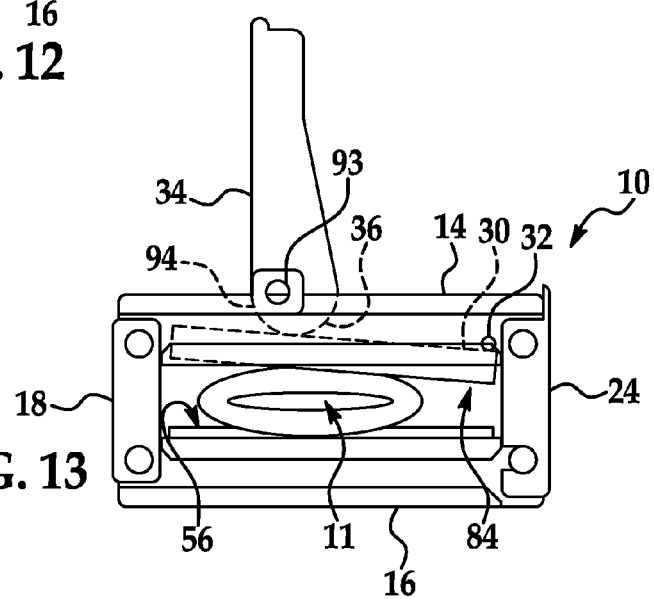
FIG. 13 is a side elevation view of the clamp of FIG. 12 having its second link engaged with its bottom member and its lever in a partially engaged position.
Figure 14:
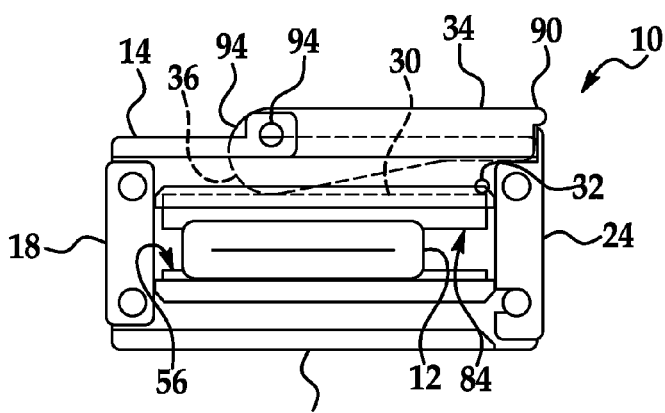
FIG. 14 is a side elevation view of the clamp of FIG. 13 having its lever in a fully engaged position.
Figure 15:
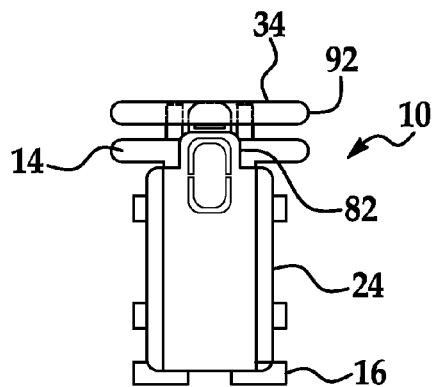
FIG. 15 is an end elevation view of the clamp of FIG. 14.
Figure 16:
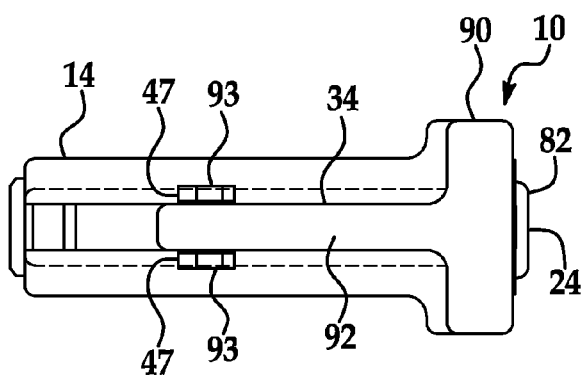
FIG. 16 is a top plan view of the clamp of FIG. 14.

The lever 34 can include a T-shaped handle 90 and a shank 92 extending toward the hinge 33 as shown in FIG. 16. The proximal end of the shank 92 can include a pair of pins 93 extending through the apertures 49 in the flanges 47 of the top member 14. The lever 34 can be coupled to the flanges 47 by forming the lever 34 of a resilient material and snapping the pins 93 into engagement with the flanges 47. The shank 92 can have a width less than the distance between the sidewalls 38 and 40 of the top member 14 such that the shank 92 can fit between the sidewalls 38 and 40 when the lever 34 is engaged as shown in FIG. 5. Additionally, the handle 90 can fit snuggly against the tab 82 of the second link 24 when the lever 34 is engaged as shown in FIG. 3. The cam portion 36 of the lever 34 can extend further from a rotation axis of the lever 34 (i.e., an axis passing axially through the pins 93) than a bottom portion 94 of the lever 34 as shown in FIG. 12. Thus, the lever 34 can exert a greater downward force on the guillotine 30 as the lever 34 is rotated as shown in FIGS. 12-14, and thus rotation of the lever 34 can cause the guillotine 30 to exert a downward force on the tube 12. The cam portion 36 can be of sufficient size to urge the guillotine 30 downward as shown in FIG. 14 to fully close the tube 12.

The clamping sequence performed using the clamp 10 is shown in FIG. 12-14 beginning with the top and bottom members 14 and 16 parallel and partially closing the tube 12 as shown in FIG. 12 and ending with the tube 12 fully closed as shown in FIG. 14. Using the lever 34 to urge the guillotine 30 downward to close the tube 12 provides a mechanical advantage as a result of the distance between the handle 90 of the lever 34 and the pins 93 compared to the distance between the cam portion 36 of the lever 34 and the pins 93 as can be seen in FIG. 14. The clamp 10 provides another mechanical advantage in that there is a relatively long distance between where the cam portion 36 contacts the guillotine 30 and the hinge 33 as shown in FIGS. 13 and 14. As a result, the force required to fully close the tube 12 can be sufficiently low that the clamp 10 can be operated by hand without much difficulty.

Alternatively, the clamp 10 can vary from the example described above. For example, instead of forming pins 48 and 62 that are integral with the top and bottom member 14 and 16, respectively, separate pins can be inserted through apertures in the top and bottom members 14 and 16. As another example, instead of the slots 80 held in engagement with the pins 48 and 62 due to friction between the second link 24 and bottom member 16, the slots 80 can be formed to engage the pins 48 and 62 with a snap-fit. As still another example, instead of the hinge 32 that prevents movement of the guillotine 30 in an upward direction as shown in FIGS. 13 and 14, a stop or other structure can be used to limit the upward movement of the guillotine 30. As still yet another example, a different structure can be used to provide a mechanical advantage for closing the tube 12. An example of such a different structure is the lever 34 including a ratchet portion at its proximal end, and the guillotine 30 including a vertically oriented rack of gear teeth engaged with the ratchet portion of the lever 34 for vertical movement of the guillotine in response to rotation of the lever 34.

The clamp 10 can offer many advantages. As an example of an advantage of the clamp 10, the clamp 10 can be installed on the tube 12 even if the tube 12 is of the over-sized variety without requiring an amount of force greater than that which can be applied by hand without significant straining (e.g., without the user having to apply his bodyweight to the clamp 10). As another example of an advantage of the clamp 10, the clamp 10 can be installed on an intermediate portion of the tube 12 without having to thread the clamp 10 onto an end of the tube 12.

Figure 18:
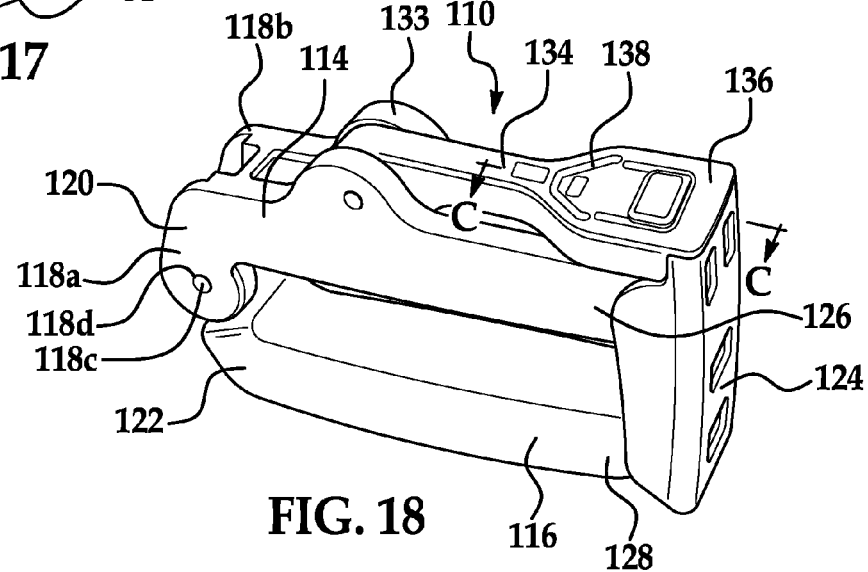
FIG. 18 is a perspective view of another example of a tube clamp.
Figure 19:
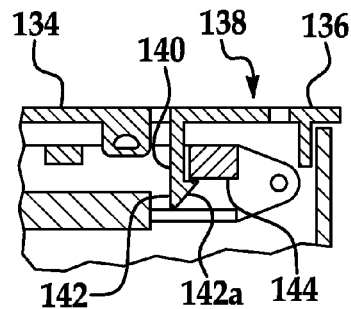
FIG. 19 is a partial cross sectional view taken along the line C-C shown in FIG. 18.

Another example of a clamp 110 is shown in FIGS. 18 and 19. Referring first to FIG. 18, the clamp 110 can include a top member 114 rotatably coupled to a bottom member 116. The top and bottom members 114 and 116 can have similar structures as the top and bottom members 14 and 16 with the exception of a few differences. One such difference can be that instead of being rotatably coupled by the first link 18, first ends 120 and 122 of the top and bottom members 114 and 116, respectively, can define a hinge 118. For example, the first end 120 of the top member 114 can define two spaced apart sidewalls 118a and 118b, and the bottom member 116 can define a pin 118c extending through apertures 118d in the two sidewalls 118a and 118b. A second link 124 similar to the second link 24 can be rotatably coupled to a second end 126 of the top member 114 and engagable with a second end 128 of the bottom member 118. A lever A lever 134 can be coupled to a hinge 133 that is similar to the hinge 33, and the lever 134 can include a cam portion for actuating a guillotine carried by the top member 114 in a similar fashion as to how the cam portion 36 actuates the guillotine 30 carried by the top member 14.

Figure 20:
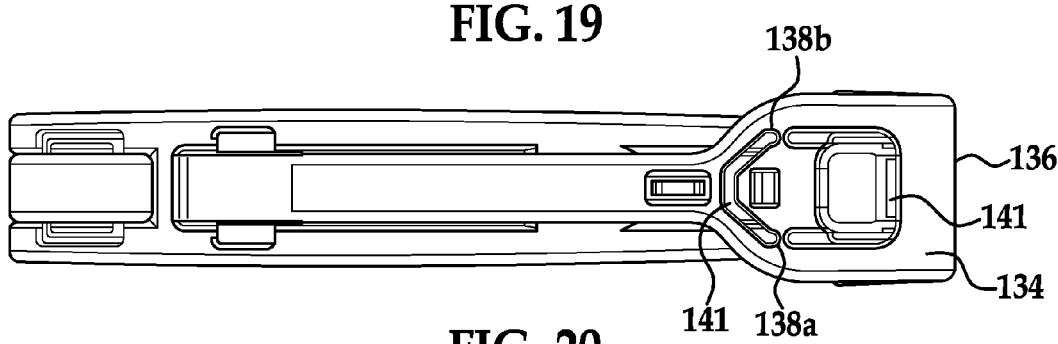
FIG. 20 is a partial top plan view of a lever of the tube clamp of FIG. 18.

Another difference between the clamps 10 and 110 is that the lever 134 can become automatically locked in engagement with another portion of the clamp 110, such as the top member 114 or second link 124, in response to being rotated into an actuated position shown in FIG. 18 in which the cam portion actuates the guillotine. For example, as shown in FIGS. 18-20, a distal end 136 of the lever 134 can define a button 138. The button 138 can be rotatable about an axis, e.g., an axis parallel to an axis of rotation of the lever 134 about the hinge 133. An example of the button 138 shown in FIG. 20 can be connected to a remaining portion of the lever 134 by two tabs 138a and 138b, and spaces 141 can be defined between the button 138 and the remaining portion of the lever 134.

Referring to FIG. 19, a projection 140 can extend from a side of the button 138 facing the bottom member 116 and can include a barb 142 at its distal end opposite the button 138. The barb 142 can include an angled surface 142a such that the surface 142a contacts a crossmember 144 extending between two sidewalls of the top member 114 during rotation of the lever 134 into the actuated position. The angle of the surface 142a can allow the barb 142 to produce a force urging the projection 140 and/or button 138 to rotate such that the barb 142 is allowed to slide past the crossmember 144. Once the barb 142 slides past the crossmember 142, the barb 142 can engage a side of the crossmember 144 facing the bottom member 116 as a result of, for example, tubing 12 compressed between the top and bottom members 114 and 116 urging the members 114 and 116 away from one another. With the barb 142 engaged with the crossmember 144, the top member 114 is locked in the actuated position. To release the top member 114 from the actuated position, the button 138 can be rotatable in the direction indicated by the arrow shown in FIG. 19 as a result of being compressed by, for example, a finger or thumb of an operator. Rotation of the button 138 in the direction indicated in FIG. 19 can move the barb 142 such that it does not engage the crossmember 144, and the force created by compressed tubing 12 between the top and bottom members 114 and 116 can urge the members 114 and 116 away from one another.

While an automatic locking feature is shown as including the button 140 and the projection 140 with its barb 142, other automatic locking structures can be used. For example, one or more projections with barbed distal ends can extend upward from the top member 114 for engagement with a portion of the lever 114 when the lever is moved into the actuated position. As another example, the lever 134 can include a barbed projection that engages the second link 124 instead of the top member 114.

The clamp 110 can offer the same advantages as the clamp 10. Additionally, the clamp 110 can allow the top member 114 to be automatically lockable in response to being moved into an actuated position relative to the bottom member 114, and the automatic lock can be selectively disengaged.

Figure 21A:
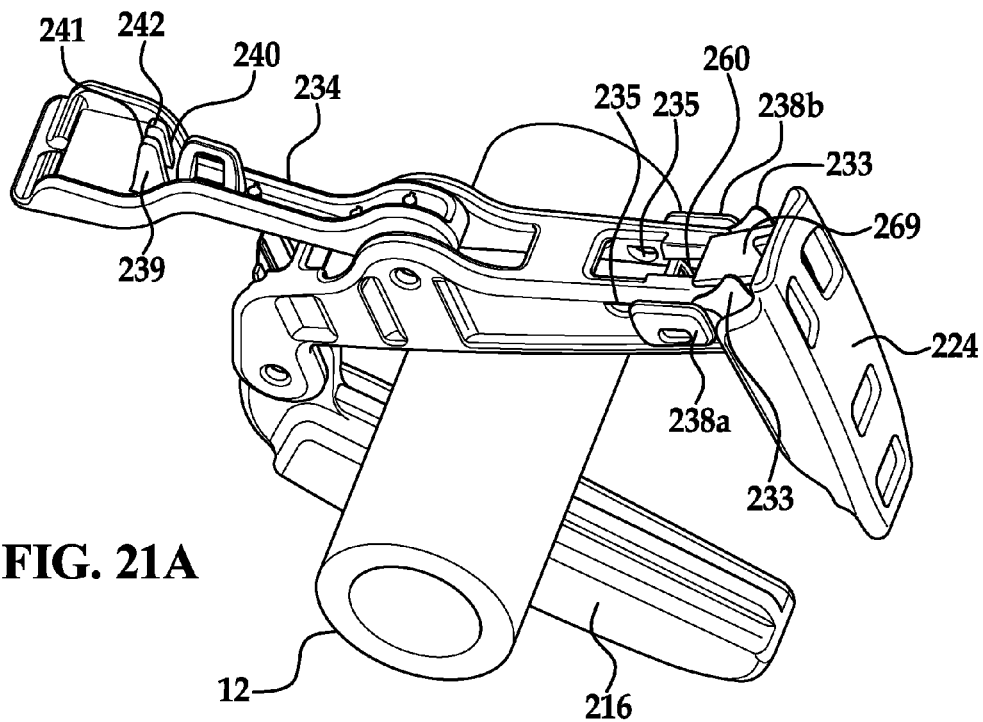
FIGS. 21A-B are perspective views of another example of a tube clamp and a tube or tubes in an unengaged position.

Another example of a clamp 210 is shown in FIGS. 21A-29, which can offer the same advantages as the clamp 10 and 110. FIGS. 21A, 21B, and 22 illustrate the clamp 210 in an unengaged position and FIGS. 23-29 illustrate the clamp 210 in an engaged position (without the tube 12). The clamp 210 can include a top member 214 rotatably coupled to a bottom member 216. The leverage of bottom member 216 can permit the clamp 210 to restrict the fluid flow in, for example, heavy wall tubing similar to that shown in FIG. 1. Similar to the coupling of top and bottom members 114 and 116, first ends 220 and 222 of the top and bottom members 214 and 216, respectively, can define a hinge 218. For example, the first end 220 of the top member 214 can define two spaced apart sidewalls 218a and 218b, and the bottom member 216 can define a pin 218c extending through apertures 218d in the two sidewalls 218a and 218b.

Figure 21B:
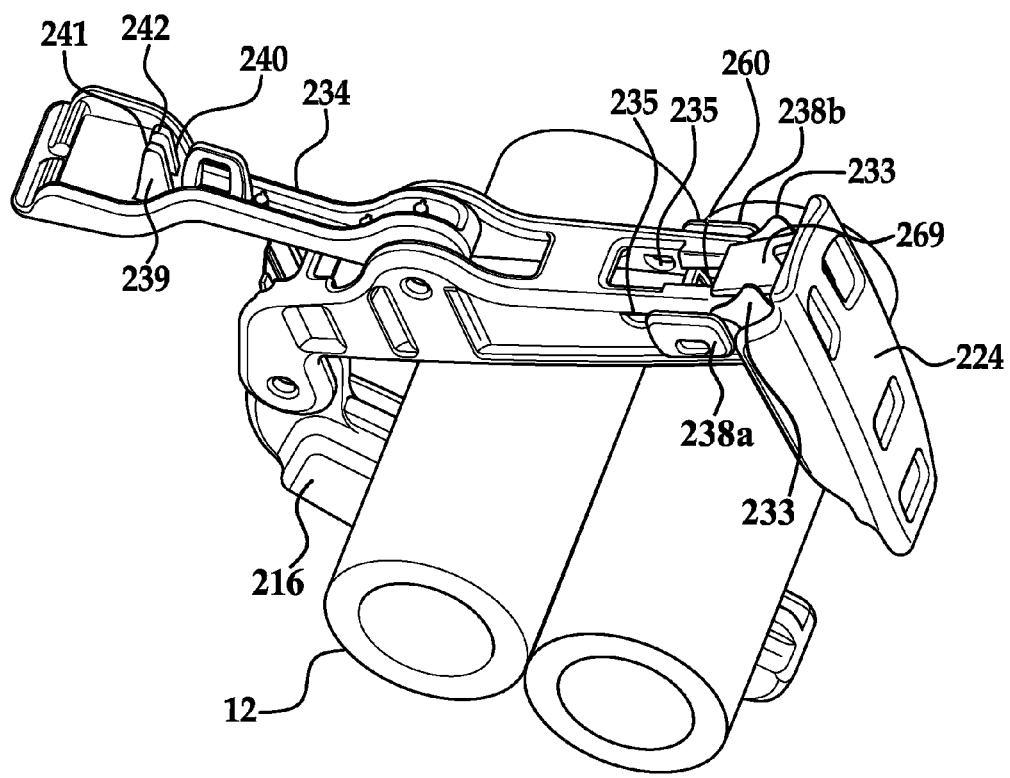
Figure 24:
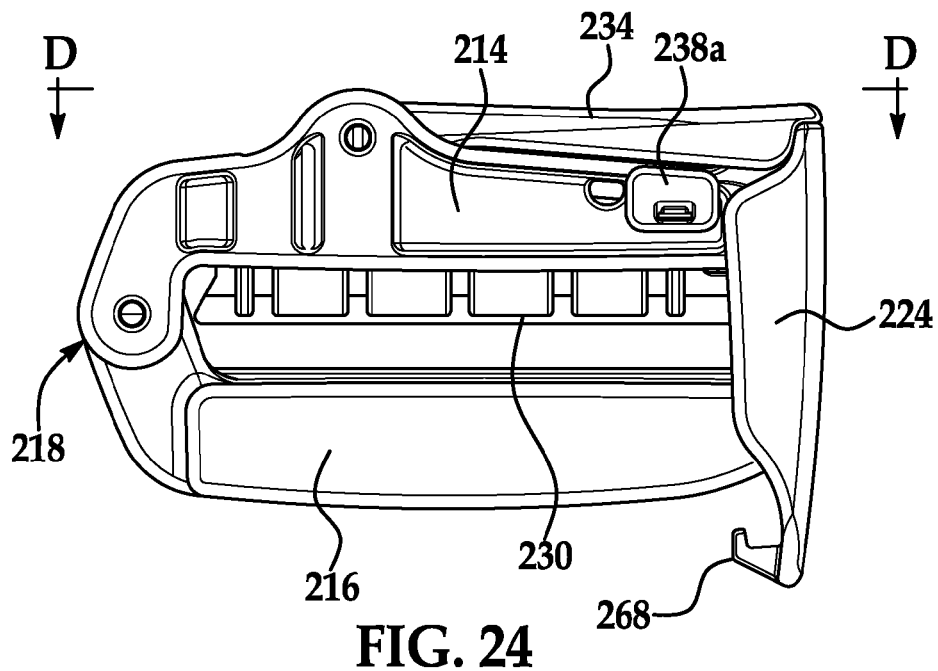
FIG. 24 is a side elevation view of the clamp of FIG. 23.
Figure 25:
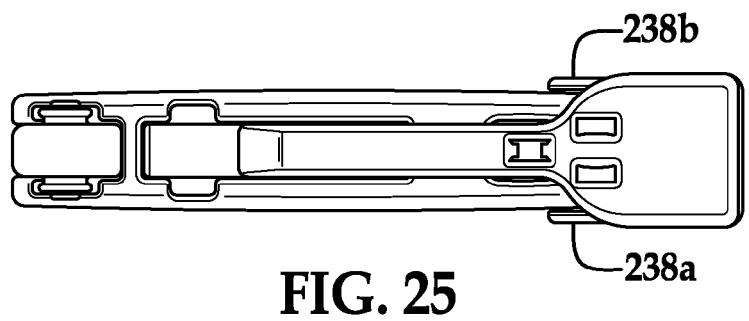
FIG. 25 is a top plan view of the clamp of FIG. 23.
Figure 26:
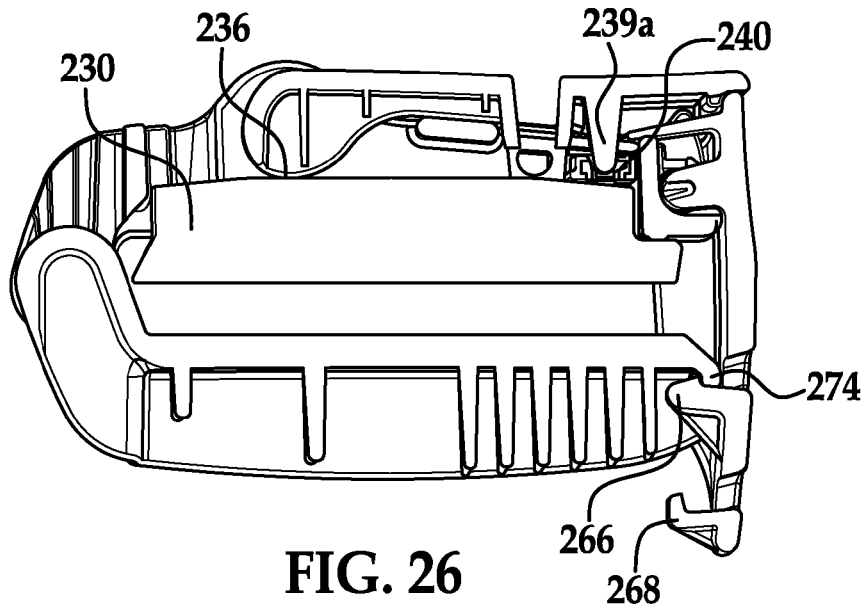
FIG. 26 is a cross-section of the clamp taken along line D-D of FIG. 24.
Figure 27:
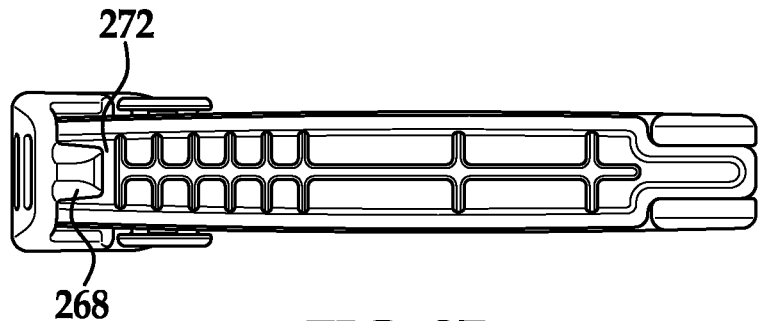
FIG. 27 is a bottom plan view of the clamp of FIG. 23.
Figure 28:
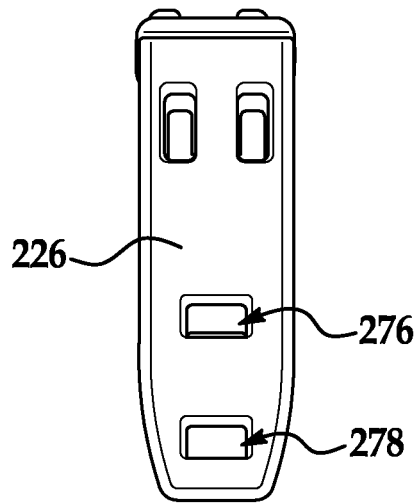
FIG. 28 is an end elevation view of the clamp of FIG. 23.
Figure 29:
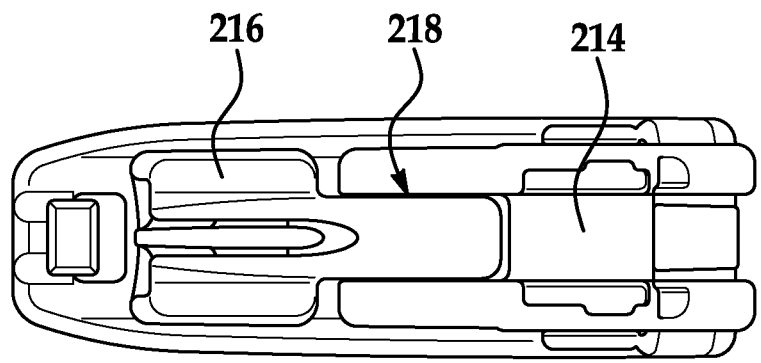
FIG. 29 is another end elevation view of the clamp of FIG. 23.

A link 224 can be rotatably coupled to a second end 226 of the top member 214 and engagable with a second end 228 of the bottom member 218. Two stop members 233 extend from the top member 214 that assist in preventing the link 224 from over-travel. A lever 234 can be coupled to a hinge 233 that is similar to the hinge 133, and the lever 234 can include a cam portion 236 for actuating a guillotine 230 carried by the top member 214 in a similar fashion as to how the cam portion 36 actuates the guillotine 30 carried by the top member 114. Guillotine 230 may also be interchangeable with other guillotine members that can accommodate tubing of, as discussed previously, different inner and outer diameters. Although only one tube is shown in FIG. 21A, clamp 210 can be capable of clamping multiple tubes at one time as shown in FIG. 21B.

As shown in FIGS. 23-29, the lever 234 is automatically locked in engagement with with the top member 214 although the lever 234 may be automatically locked in engagement with another portion of the clamp 210 such as second link 224. The lever 234 is automatically locked in response to being rotated into an actuated position shown in which the cam portion 236 actuates the guillotine 230. The top member 214 can also include safety lockout holes 235 that can be used in conjunction with, for example, a cable tie (not shown) to prevent the lever 234 from being unlocked once it has been rotated into the actuated position. The operator can thread the cable tie through the holes 265 and secure it tightly around the lever 234. Of course, other types of fasteners can be used to prevent the lever from being unlocked, which may or may not make use of the holes 265.

Unlike previous embodiments, the clamp 210, as shown in FIGS. 21A-27, can include buttons 238a and 238b (e.g. pushbuttons) at the second end 236 of top member 210. Upon rotation into the engaged position, two projections 239 and 240 extending from lever 234 and facing the bottom member 216 can be inserted into a mating hole 260. Mating hole 260 is formed by two arms 250a and 250b laterally extending from button 238a and two arms 252a and 252b laterally extending from button 238b. The arms 250a and 250b have a sidewall 260a extending therebetween forming a first wall 260a of mating hole 260. The arms 252a and 252b have a sidewall 250b extending therebetween forming a second sidewall 260b of mating hole 260. Extending through an inner portion of the arm 252a is a recess (not shown) that is shaped to slidably receive arm 250a. Similarly, extending through an inner portion of the arm 252b is a recess shaped to slidably receive arm 252a. The mating of arms 250a and 252a and the mating of arms 250b and 252b form a third sidewall 260c and a fourth sidewall 260d, respectively, of mating hole 260.

Projections 239 and 240 each include a barb 241 and 242, respectively at the distal end thereof. The barbs 241 and 242 each have an angled surface 239a and 240a, respectively. The angle of the surfaces 239a and 240a can allow the barbs 241 and 242 to produce a force urging the buttons 238a and 238b to expand away from one another such that the barbs 241 and 242 are allowed to slide past the sidewalls 260a and 260b, respectively. Specifically, the arm 250a and the arm 252a slidably extend outward in opposing directions and at the same time and the arm 250b and the arm 252b slidably extend outward in opposing directions. Once the barb 241 slides past the sidewall 260a, the barb 241 can engage a side of the button 238a facing the bottom member bottom member 216. Similarly, once the barb 242 slides past the sidewall 260b, the barb 242 can engage a side of the button 238b facing the bottom member 216. With the barbs 241 and 242 engaged within mating hole 260, the top member 214 is locked in the engaged position. Once the clamp 210 is in the engaged position, the clamp, for example, will not open, unless the lever 234 is unlocked.

To release the top member 114 from the engaged position, the buttons 238a and 238b can be inwardly and simultaneously pressed, for example, by a finger and a thumb of an operator. Pressing of the buttons 238a and 238b results in a force that causes the arm 250a and the arm 252a to slidably extend toward one another and, at the same time, and causes the arm 250b and the arm 252b to slidably extend toward one another thereby permitting the barbs 241 and 242 to disengage from the sides of buttons 238a and 239b, respectively, facing the bottom member 216. The link 224 can then be pulled from the bottom member 216, thereby permitting the tube 12 to be removed.

Similar to the previous embodiments, when link 224 is not engaged with the bottom member 216, as shown in FIG. 1, the top member 214 can be rotated relative to the bottom member 216. To engage the clamp 210 with the tube 12, the top member 214 can be rotated away from the bottom member 216 such that there is a sufficient distance between the top and bottom members 214 and 216 to insert the tube 12 therebetween. With the top and bottom members 214 and 216 rotated sufficiently apart from one another, the clamp 210 can be moved to position the tube 12 between the top and bottom members 214 and 216, and then the top member 214 can be rotated toward the bottom member 216.

The link 224 can be engaged with the second end 228 of the bottom member 216 to hold the top and bottom members 214 and 216 in a relatively parallel position. The bottom member 216 can be engaged to one of two curved hook members 266 and 268. Hook member 266 permits clamp 210 to be in a first engaged position ("stop flow position"), hook member 268 permits clamp 210 to be in a second engaged position ("start flow position"). In both positions, each of the hooks 266 and 268 is engageable with an engagement platform 272 of bottom member 216. A spring 269 extends from link 224 that can aide in closing the link back over the hook members 266 268. A curved stop member 274 extends from the platform 272 to maintain the clamp 210 in either the first engaged position or the second engaged position. Using the lever lever 234, the operator can control the amount of fluid flowing through tube 30. In general, the more the lever 234 is rotated toward the top member 214 in the actuate position, the more the guillotine 230 closes on the tube. As the guillotine 230 closes on the tube, the fluid flow decreases accordingly. Conversely, if the operator desires to increase the fluid flow, the lever 234 can be rotated in away from the top member 214. The flow can be metered in both the first engaged position and the second engaged position.

The locking link 226 includes two telltale windows 276 and 278 to indicate a flow position of the clamp 210. Specifically, when the hook member 266 is engaged with the platform 272, the telltale window 276 provides the operator with a visual indicator that the clamp 210 is in the stop flow position. Similarly, when the hook member 268 is engaged with the platform 272, the telltale window 278 provides the operator with a visual indicator that the clamp 210 is in the start flow position.

While examples of clamps have been described in connection with what are presently considered to be the most practical examples, it is to be understood that the invention is not to be limited to the disclosed examples but, on the contrary, is intended to cover various modifications and equivalent arrangements included within the scope of the appended claims, which scope is to be accorded the broadest interpretation so as to encompass all such modifications and equivalent structures as is permitted under the law.

The invention claimed is:
1. A clamp for compressing a flexible tube, comprising:
 a first member;
 a second member moveably coupled to the first member and adapted to move into and out of a clamping position to apply a compressive force to the tube, at least one of the first and second members including a pair of sidewalls that define a channel;
 a locking member adapted to hold the first and second members in a fixed clamping position, wherein rotation of the first member relative to the second member is prevented;
 a third member moveably retained in the channel, the third member adapted to move from a first position to a second non-parallel position relative to the first position; and
 a fourth member moveably coupled to one of the first member and the second member, wherein the fourth member is adapted such that, when the first and second members are held in the fixed clamping position by the locking member, the fourth member is adapted to engage with the third member such that the third member moves from the first position to the second non-parallel position to apply an additional compressive force to the tube.

2. The clamp of claim 1, wherein the first member and the second member each have a first end and an opposing second end, wherein the locking member is rotatably coupled to one of the second end of the first member and the second end of the second member, and wherein the locking member is engageable with the other one of the second end of the first member and the second end of the second member.

3. The clamp of claim 2, wherein the first member and second member are connected at their first ends by one of a connecting member and a second hinge.

4. The clamp of claim 1, wherein the channel defined by the pair of sidewalls is adapted to permit upward and downward movement of the third member.

5. The clamp of claim 4, wherein the third member is retained in the channel by a first hinge adapted to limit the upward movement of the third member.

6. The clamp of claim 1, wherein the third member has a first end and an opposing second end, a first hinge coupling the third member to the first or second member at the first or second end of the third member such that the third member rotates about the first hinge when the fourth member engages with the third member to apply the additional compressive force to the tube.

7. The clamp of claim 1, wherein the third member includes a longitudinally extending cross-bar portion and a lower portion, the lower portion having a v-shaped edge extending substantially the entire length thereof.

8. The clamp of claim 1, wherein a platform extends substantially the entire length between the pair of sidewalls and a ridge extends substantially the entire length of the platform.

9. The clamp of claim 1, wherein the fourth member is adapted to lock with one of the first and second members.

10. The clamp of claim 1, wherein the fourth member includes a rotatable button and at least one projection extending from a bottom surface of the button, the at least one projection having a barbed end adapted to engage a crossmember when the fourth member is rotated into the clamping position.

11. The clamp of claim 1, wherein the fourth member includes at least one projection extending from a bottom surface of the fourth member and one of the first and second members includes first and second pushbuttons extending from opposites sides therefrom, the first and second pushbuttons each having a pair of arms adapted to form a hole, the at least one projection having a barbed end adapted to engage a portion of the hole when the fourth member is rotated into the clamping position.

12. The clamp of claim 1, wherein the third member includes at least one hook member, the hook member adapted to engage with one of the first and second members.

13. The clamp of claim 1, wherein the third member includes at least one telltale window, the telltale window adapted to indicate a flow position of the clamp.

14. A clamp for compressing a flexible tube, comprising:
a first member having a first end and a second end;
a second member with a first end and a second end, the first and second members moveably coupled at their first ends and adapted to move into and out of a clamping position to apply a compressive force to the tube;
a locking member pivotally coupled to the second end of at least one of the first member and second member, the locking member adapted to hold the first and second members in a fixed clamping position, wherein the locking member is moveably coupled to one of the first and second members by a first hinge;
a lever member moveably coupled to one of the first member and the second member; and
a guillotine moveably retained in a channel defined by a pair of sidewalls of one of the first member and the second member at a second hinge attached to the guillotine, wherein the channel defined by the pair of sidewalls is adapted to permit upward and downward movement of the guillotine and wherein a lip inwardly extends from at least one of the pair of sidewalls, the lip adapted to limit the downward movement of the guillotine, the lever adapted to engage the guillotine to apply and additional compressive force to the tube when the first and second members are held in the fixed clamping position.

15. A method for compressing at least one flexible tube, the method comprising:
positioning the at least one tube between a first member and a second member of a clamp, the clamp comprising:
the first and second members, the second member moveably coupled to the first member,
a locking member,
a third member moveably retained in a channel defined by a pair of sidewalls of one of the first member and the second member, the third member adapted to move from a first position to a second non-parallel position relative to the first position; and
a fourth member moveably coupled to one of the first member and the second member;
rotating the first member toward the second member to a clamping position such that an initial compressive force is applied to the at least one tube;
engaging the locking member such that the first and second members are held in a fixed clamping position, wherein rotation of the first member relative to the second member is prevented; and
while the first and second members are held in the fixed clamping position, rotating the fourth member to engage the third member such that the third member moves from the first position to the second non-parallel position and an additional compressive force is applied to the at least one tube.

16. The method of claim 15, further comprising:
rotating the fourth member to control the flow of fluid through the at least one tube.

17. The method of claim 15, wherein the locking member is rotatably coupled to one of the first and second members and includes at least two hook members, wherein engaging the locking member comprises at least one of:
engaging a first one of the at least two hook members with the other of the first and second members such that the at least one tube is in a stop flow position; and
engaging a second one of the at least two hook members with the other of the first and second members so that the at least one tube is in a start flow position.

18. The method of claim 15, further comprising:
interchanging the third member with a different member.

19. The method of claim 15, wherein the fourth member includes a rotatable button and at least one projection extending from a bottom surface of the button, the at least one projection having a barbed end and wherein one of the first and second members includes a crossmember and wherein rotating the fourth member to the clamping position includes:
engaging the barbed end of the at least one projection with the crossmember to secure the fourth member.

20. The method of claim 19, further comprising:
pressing the button to disengage the barbed end from the cross member to release the fourth member.

21. The method of claim 18, wherein the fourth member includes at least one projection extending from a bottom surface of the fourth member and one of the first and second members includes first and second push buttons extending from opposites sides therefrom, the first and second pushbuttons each having a barbed end and wherein rotating the fourth member to the clamping position includes:
engaging the barbed end with a portion of the hole to secure the fourth member.

22. The method of claim 21, further comprising:
simultaneously pressing the first and second pushbuttons to disengage the barbed end from the hole to release the fourth member.

23. The method of claim 15, wherein the at least one tube includes a plurality of tubes, the method further comprising:
positioning the plurality of tubes between the first and second members;
rotating the first member toward the second member to the clamping position such that the initial compressive force is applied to the plurality of tubes;
engaging the locking member such that the first and second members are held in the clamping position;
rotating the fourth member to engage the third member such that the additional compressive force is applied to the plurality of tubes.

* * * * *